United States Patent
Burns et al.

(10) Patent No.: US 9,417,189 B2
(45) Date of Patent: Aug. 16, 2016

(54) FLUORESCING GEL FORMULATIONS AND THEIR APPLICATIONS

(71) Applicant: Ecolab USA Inc., St. Paul, MN (US)

(72) Inventors: Nicole Burns, Elko, MN (US); Xin Sun, Eagan, MN (US); Thomas R. Mohs, Eagan, MN (US); Joseph R. Wegner, Falcon Heights, MN (US); Mark Levitt, Lake Elmo, MN (US); Steven E. Lentsch, St. Paul, MN (US)

(73) Assignee: ECOLAB USA INC., St. Paul, MN (US)

( * ) Notice: Subject to any disclaimer, the term of this patent is extended or adjusted under 35 U.S.C. 154(b) by 0 days.

(21) Appl. No.: 14/453,043

(22) Filed: Aug. 6, 2014

(65) Prior Publication Data

US 2014/0346371 A1  Nov. 27, 2014

Related U.S. Application Data

(63) Continuation of application No. 13/267,705, filed on Oct. 6, 2011, now Pat. No. 8,835,874.

(60) Provisional application No. 61/391,422, filed on Oct. 8, 2010.

(51) Int. Cl.
| | |
|---|---|
| *G01N 21/64* | (2006.01) |
| *C09K 11/06* | (2006.01) |
| *C08K 5/00* | (2006.01) |
| *C08L 1/08* | (2006.01) |
| *C08L 1/28* | (2006.01) |
| *C08L 5/00* | (2006.01) |
| *C09K 11/02* | (2006.01) |

(52) U.S. Cl.
CPC .............. *G01N 21/64* (2013.01); *C08K 5/0041* (2013.01); *C08K 5/0091* (2013.01); *C08L 1/08* (2013.01); *C08L 1/28* (2013.01); *C08L 5/00* (2013.01); *C09K 11/025* (2013.01); *C09K 11/06* (2013.01); *G01N 21/643* (2013.01); *G01N 2201/061* (2013.01)

(58) Field of Classification Search
CPC ................................ G01N 21/64; C09K 11/06
USPC .......................... 250/459.1, 492.1; 252/301.21
See application file for complete search history.

(56) References Cited

U.S. PATENT DOCUMENTS

| | | | |
|---|---|---|---|
| 3,871,898 | A | 3/1975 | Reinert et al. |
| 5,234,617 | A | 8/1993 | Hunter et al. |
| 5,688,930 | A | 11/1997 | Bertho et al. |
| 5,948,153 | A | 9/1999 | Ann et al. |
| 6,274,874 | B1 | 8/2001 | Sidhu |
| 7,718,395 | B2 | 5/2010 | Carling |
| 8,308,198 | B2 | 11/2012 | Udagawa et al. |
| 2001/0026942 | A1 | 10/2001 | Carpenter et al. |
| 2002/0022585 | A1 | 2/2002 | Morelli et al. |
| 2006/0079438 | A1 | 4/2006 | Brush et al. |
| 2006/0223731 | A1 | 10/2006 | Carling |
| 2007/0143032 | A1 | 6/2007 | Wieringa et al. |
| 2009/0208051 | A1 | 8/2009 | Emo et al. |
| 2009/0223635 | A1 | 9/2009 | Lawless |
| 2009/0237651 | A1 | 9/2009 | Arndt et al. |
| 2009/0261270 | A1 | 10/2009 | Carling |
| 2009/0325308 | A1 | 12/2009 | Harada |

FOREIGN PATENT DOCUMENTS

| | | |
|---|---|---|
| JP | 10204489 | 8/1998 |
| JP | 2001246339 | 9/2001 |
| JP | 2009210514 | 9/2009 |
| WO | 9913833 | 3/1999 |
| WO | 0006090 | 2/2000 |

OTHER PUBLICATIONS

Ecolab USA Inc. et al., PCT/US2011/055154 filed Oct. 6, 2011, International Search Report and Written Opinion of the International Searching Authority mailed May 29, 2012.
Abstract of JP 1100442(A), Hitachi Ltd., 1 page, published Apr. 18, 1989.
Abstract of JP 63073140(A), Hitachi Ltd., 1 page, published Apr. 2, 1988.
Abstract of JP 10292199(A), Lion Corp., 1 page, published Nov. 4, 1988.
Barber, J.A.S. et al., "Fluorescent tracer technique for measuring the quantity of pesticide deposited to soil following spray applications" Crop Protection 22 (2003), 15-21, Dec. 31, 2003.
Bergervoet, P.W.M. et al., "Application of the forensic Luminol for blood in infection control", Journal of Hospital Infection (2008) 68, 329-333, Dec. 31, 2008.
Carling, Philip, "Environmental hygiene: new understanding and challenges" Private Hospital Healthcare Europe Sep. 2008. 7 pages, Dec. 31, 2008.
Carling, Philip C. et al., "Improved Cleaning of Patient Rooms Using a New Targeting Method" Clinical Infectious Diseases, 2006, pp. 285-288, Dec. 31, 2006.
Carling, Philip C. et al., "Improving Cleaning of the Environment Surrounding Patients in 36 Acute Care Hospitals", Infection Control and Hospital Epidemiology, Nov. 2008, vol. 29, No. 11, pp. 1035-1041, Nov. 30, 2008.

(Continued)

*Primary Examiner* — David Porta
*Assistant Examiner* — Faye Boosalis
(74) *Attorney, Agent, or Firm* — McKee, Voorhees & Sease, PLC

(57) ABSTRACT

Fluorescing gel formulations are disclosed for monitoring cleaning of a surface. The fluorescing gel formulations are stable, fluoresce under UV light, and do not leave a mark after drying and removal. The compositions include an oppositely charged complexing agent which is used in combination with an anionic or cationic optical brightener. In some embodiments, the compositions include a cationic optical brightener with no complexing agent.

17 Claims, No Drawings

(56) References Cited

OTHER PUBLICATIONS

Griffith, C. J. et al., "An evaluation of hospital cleaning regimes and standards", Journal of Hospital Infection (2000) 45:19-28, Dec. 31, 2000.
Hartel, Peter G. et al., "Exposing water samples to ultraviolet light improves fluorometry for detecting human fecal contamination", Water Research 41 (2007), pp. 3629-3642, Dec. 31, 2007.
Lipscomb, I.P. et al., "Rapid method for the sensitive detection of protein contamination on surgical instruments", Journal of Hospital Infection (2006), 62, pp. 141-148, Dec. 31, 2006.
Lu, Y.F. et al., "Laser surface cleaning and real-time monitoring", Proceedings of SPIE vol. 4070 (2000), pp. 331-337, Dec. 31, 2000.
Pyrek, Kelly M., "Hospitals Can learn From CSI Sleuthing Methods" Infection Control Today, http://www.infectioncontroltoday.com/PrinterFriendly.aspx?id={CB330C85-691A-4D5C . . . retrieve from the Internet on Dec. 15, 2011.
Salo, Satu et al., "Cleaning validation of fermentation tanks", Food and Bioproducts Processing 86 (2008) pp. 204-210, Dec. 31, 2008.
NHS Supply Chain, "Cleanser alcohol hand rub training get Fluorescent gel 500 ml bottle with integral pump dispenser" MRB 180, Brochure, 2 pages, https://my.supplychain.nhs.uk/catalogue/product/mrb180/cleanser-alcohol-hand-rub-training-gel-fluorescent-gel-500ml-bottle-with-integral-pump-dispenser, retrieved online on Mar. 25, 2011.
European Patent Office, "extended European Search Report" issued in connection with International Application No. PCT/US2011/055154, 5 pages, mailed Jun. 2, 2014.

FLUORESCING GEL FORMULATIONS AND THEIR APPLICATIONS

CROSS-REFERENCE TO RELATED APPLICATIONS

This application is a continuation application of Ser. No. 13/267,705 filed Oct. 6, 2011, which claims priority under 35 U.S.C. §119 of a provisional application Ser. No. 61/391,422 filed Oct. 8, 2010, and which application is hereby incorporated by reference in its entirety.

TECHNICAL FIELD

The present invention relates to monitoring cleaning of surfaces, and, more particularly, to monitoring cleaning of surfaces in health care or food service environments.

BACKGROUND OF THE INVENTION

Although environmental cleaning and disinfecting practices have become a cornerstone of patient care, assessment of actual compliance with such procedures has not been reported. During the past decade controlling and limiting the spread of health care associated pathogens has become one of the most challenging aspects of health care epidemiology. Unfortunately the continuing escalation of infections with these pathogens has led to more than 1.5 million people developing resistant hospital acquired, i.e., nosocomial, infections in the U.S. annually. Despite enhancement of hand hygiene through the development of user friendly alcohol based hand cleansers, the manner in which they are used and the difficulty achieving appropriate compliance with their use potentially limit their effectiveness.

Three pathogens posing significant nosocomial problems are MRSA (Methicillin Resistant *Staphylococcus aureus*), VRE (Vancomycin Resistant *Enterococcus*), and *Clostridium difficile* (*C. difficile*). Their importance derives from a combination of resistance to presently available treatments and an ability to rapidly spread extensively in the environment around hospitalized patients. MRSA is present in wound infections, as associated with bed sores and catheters. VRE is present in bowel and urinary tract infections. *C. difficile* is also present in bowel infections and presents as severe diarrhea. For each of these pathogens, control with present antibiotics is problematical, if not impossible.

Although screening based isolation practices have been advocated to limit the transmission of MRSA and VRE, there are logistical issues and concerns about the practical application and cost effectiveness of such practices. Reliance on such practices may alter the epidemiology but not the incidence of health care associated infections. Additionally, outbreak persistence as well as significant environmental contamination occurs despite patients being on isolation for VRE and MRSA as well as for patients who are asymptomatically colonized with *C. difficile* for which screening is not feasible. These programmatic as well as pathogen based issues clearly have limited the effectiveness of current as well as proposed isolation practices.

Enhancement of existing cleaning and disinfection practices deserves further consideration and evaluation. Although it is not currently feasible to define the independent role of the hospital environment in the transmission of health care associated pathogens except in isolated investigations, numerous studies over the past twenty years have confirmed the frequent contamination of many surfaces in the near patient environment with hospital associated pathogens able to survive on inanimate surfaces for weeks to months.

With respect to individual pathogens, it has been found that high rates of environmental contamination with *C. difficile* have been associated both with symptomatic as well as asymptomatic patients. Direct evaluation of the role of environmental contamination in the transmission of *C. difficile* found a strong correlation with the intensity of environmental contamination, and outbreaks of *C. difficile* infection have been successfully terminated by enhanced cleaning/disinfecting activities.

The role of environmental contamination in transmission of VRE has been documented. Recent studies have confirmed the frequency of environmental contamination, shown to be highly correlated with the number of body sites colonized as well as with the intensity of gastrointestinal tract colonization. Furthermore the ease with which gloved hands can become contaminated by limited contact with a colonized patient's bed rail and bedside table the rapid recontamination of surfaces in the near patient environment with VRE despite effective daily cleaning even in the absence of diarrhea as well as the termination of a VRE outbreak in an ICU through enhanced cleaning activities support the likely importance of the environment in the epidemiology of VRE.

MRSA is frequently found in the environment of both colonized and infected patients and colonized health care workers. The pathogen can be transmitted by the gloves of health care providers and increases in concentration in the stool of colonized patients receiving broad spectrum antibiotics. Consequently, it is likely that environmental contamination plays a role in the spread of MRSA. In addition, DNA typing in three studies has supported the likely importance of environmental reservoirs in colonal MRSA outbreaks in hospitals lasting from three months to five years.

These and similar observations confirm the longstanding belief that environmental cleaning/disinfecting activities are important in providing an optimally safe environment for patients and have led to the development of specific guidelines for environmental infection control in health care facilities. The Center for Disease Control, for example, has recommended that hospitals "thoroughly clean and disinfect environmental medical equipment surfaces on a regular basis". Similarly, the Society for Health Care Epidemiology of America's position paper regarding enhanced interventions to control the spread of resistant *Staphylococcus aureus* and *Enterococcus* recommended that hospitals "ensure" that their institutional methods of disinfecting surfaces be shown to be "adequate".

Finally, the Joint Commission for Health Care Accreditation states "hospitals are expected to develop standards to measure staff and hospital performance in managing and improving the environment of care" without defining what specific resources should be utilized to carry out such activities.

In view of the above, there is a need for a non-microbiological methodology to evaluate the thoroughness with which housekeeping activities are carried out in hospitals, food service applications, and other industrial, institutional and commercial cleaning of surfaces.

SUMMARY OF THE INVENTION

The inventors have developed a composition containing a fluorescing agent that can be applied to a surface as a cleaning audit indicator and fully removed through proper cleaning technique In accordance with one aspect of the invention, a method for monitoring cleaning of a surface includes applying an amount of the fluorescing gel formulation of the invention to an area of a surface and measuring the amount remaining on the surface. The fluorescing gel formulation may be fixed to the area of the surface, as by drying. Measuring the amount of remaining formulation on the surface may include exposing the area to ultraviolet radiation.

Some embodiments may include one or more opportunities for reducing the amount of the fluorescing gel formulation whose location may be unknown to the receiver of the opportunity. Reducing the amount may be a part of cleaning the surface. The opportunity to reduce the amount of fluorescing gel formulation may be suspended at the expiration of a period of time following initiation, where the period may be a day or less, between a day and a week, or between a week and a month.

In accordance with another aspect of the invention, a composition for monitoring cleaning of a surface includes a carrier, a water soluble optical brightener, preferably which fluoresces under UV light, and a complexing agent, which serves to neutralize the charge of the optical brightener and imparts the ability of the formed complex to be removed. The optical brightener may be cationic or anionic and the resultant complexing agent will be of opposite charge. In some embodiments, the optical brightener may be a cationic optical brightener and no complexing agent is needed. The composition may also include a surfactant, a solvent, preservatives and a thickening agent. The carrier may be water and may also be a detergent. In other embodiments the fluorescing gel formulation may be fluorescent under ultraviolet radiation. In one embodiment, the components are all appropriate for food surfaces.

In accordance with a further aspect of the invention, a method for control of nosocomial pathogens includes evaluating a cleaning program for a patient-care environment within a facility, enhancing the cleaning program for the patient care environment, and comparing the enhanced cleaning program with at least one other cleaning program. In certain embodiments, evaluating a cleaning program may include training with monitoring surfaces, collecting pre-intervention data, and comparing control within the facility.

This invention may be used as a cleaning indicator for a variety of applications where one would want to look for a residual fluorescent indicator to determine the effectiveness of a cleaning program. The compositions of the invention allow for several new application methods to apply the formulation to the surface to be evaluated, for example the compositions can be made into a solid, that could take the form similar to a pink eraser, a solid pen or marker, etc. The composition also has a low viscosity and low foaming properties that enable its use for felt pad applications such as in a marker tip and the like.

DETAILED DESCRIPTION OF THE PREFERRED EMBODIMENTS

Unless otherwise indicated, and except for the specific formulations listed in the examples, all numbers expressing quantities of ingredients or reaction conditions used herein are to be understood as being modified in all instances by the term "about".

As used herein, weight percent (wt-%), percent by weight, % by weight, and the like are synonyms that refer to the concentration of a substance as the weight of that substance divided by the total weight of the composition and multiplied by 100.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities.

The term "surfactant" refers to an organic chemical that when added to a liquid changes the properties of that liquid at a surface.

"Cleaning" means to perform or aid in soil removal, bleaching, microbial population reduction, rinsing, or combination thereof.

As used herein, a solid cleaning composition refers to a cleaning composition in the form of a solid such as a powder, a particle, agglomerate, a flake, a granule, a pellet, a tablet, a lozenge, a puck, a briquette, a brick, a solid block, a unit dose, or another solid form known to those of skill in the art. The term "solid" refers to the state of the detergent composition under the expected conditions of storage and use of the solid detergent composition. In general, it is expected that the detergent composition will remain in solid form when exposed to temperatures of up to about 100° F. and greater than about 120° F. A cast, pressed, or extruded "solid" may take any form including a block. When referring to a cast, pressed, or extruded solid it is meant that the hardened composition will not flow perceptibly and will substantially retain its shape under moderate stress or pressure or mere gravity, as for example, the shape of a mold when removed from the mold, the shape of an article as formed upon extrusion from an extruder, and the like. The degree of hardness of the solid cast composition can range from that of a fused solid block, which is relatively dense and hard, for example, like concrete, to a consistency characterized as being malleable and sponge-like, similar to caulking material.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The term "actives" or "percent actives" or "percent by weight actives" or "actives concentration" are used interchangeably herein and refers to the concentration of those ingredients involved in cleaning expressed as a percentage minus inert ingredients such as water or salts.

"Terminal cleaning" refers to cleaning of a hospital room following departure of its most recent occupant and prior to the arrival of its immediately prospective occupant.

The term "black light" refers to ultraviolet or UV radiation emanating from an ultraviolet source.

The term "transparent" refers to capable of transmitting light so that objects and images beyond can be clearly perceived.

"Nosocomial infections" are infections arising from and transmitted within a hospital environment.

Cleaning of patient rooms is an ongoing process in a hospital. Each patient occupying a room may be subject to pathogens left by a prior occupant of the room and, in turn, may insert his or her specific pathogens into the room environment. An aim of room cleaning is to decrease the likelihood of the environmental transmission of infection to an occupant of the room. Some room sites are cleaned daily while others are cleaned following patient occupation. Generally, such cleaning is unsupervised. Correlation of the health of room occupants could provide an indication of the quality of the cleaning, although with significant effort and with significant delay.

Embodiments of the invention as discussed below illustrate where monitoring may provide timely assessment as to whether current cleaning activities are consistent with control over nosocomial infections and may have the potential for objectively evaluating cleaning and disinfecting activities in various health care settings. A nontoxic composition containing an indicator material which fluoresces with exposure to a black light is inconspicuous yet may be readily removed by housekeeping products. Small volumes of composition may be confidentially applied to target sites in patient rooms following terminal cleaning and the targets reevaluated following terminal cleaning after several patients have occupied the room.

In an example, evaluation of housekeeping practices at three hospitals have confirmed high rates of cleaning of traditional sites but poor cleaning of many sites which have significant potential for harboring and transmitting microbial pathogens. An integrated program may identify such deficiencies in hospital cleaning and target remediation efforts so as to accelerate reduction in pathogen levels.

For example a hospital room typically comprises a bed in association with bed rails, bed tray, drape, and drape support. Patient call box and telephone are generally located proximal to the bed and provide communication, where telephone rests on a table. A chair often is present and provides additional seating. A sink including a faucet, handles, and bedpan flushing device, can provide a cleansing facility. A toilet containing a seat and handle resides in the patient bathroom. A grab bar provides support for patient in using the toilet. Entry into room and bathroom is through doors typically via engagement of a handle or push plate. Room lights may adjusted by a room light switch mounted on room light switch plate. Bathroom lights may be adjusted by bathroom light switch mounted on bathroom light switch plate.

Targets for monitoring are those with correspond to areas of a surface and may be chosen on the basis of the recommendation from the CDC that enhanced cleaning activities should be directed at "high touch" objects (HTOs), as well on reports in the literature of sites reported as being frequently contaminated with hospital associated pathogens. Such targets may include toilet handle, horizontal surface of toilet bowl, bedpan flushing device, horizontal surface of the sink adjacent to the faucet, doorknob or door handle, [or push/grab plate], toilet area hand hold immediately adjacent to the toilet, bedside table, telephone receiver, call button, overbed table, seat target of patient chair, bedrail adjacent to the head of the bed, drape, room light switch, and bathroom light switch.

To the degree possible, targets may be placed on the object to be monitored in an area which is easily accessible for cleaning and in close proximity to the portion of the object most frequently contaminated by patients' and health care workers' hands. As a consequence of this separation, indicator material placed on the targets is not subject to removal by the actions of the patient during the interval between placement of the indicator and the subsequent examination of the target. In addition, proximity of the targets to areas subject to patient contact makes probable that cleaning of the targets correlates with cleaning of the patient contact areas. For example a toilet handle target that is separated from, but in the proximity of, region, the area most likely to receive patient contact during use and be contaminated.

The invention may optionally include and is controllably applied to the target by an applicator or applicator system. The compositions of the invention allow for a broad range of applications including foam pad applicator, felt tip applicator (similar to a highlighter), brush, roll, wipe, and potentially a solid form to allow for an eraser style, solid pen, chalk like, etc. The applicator may be a plastic squeeze bottle. The formulations of the invention have a viscosity that allows for other methods of application which were not previously acceptable for currently available formulations, such as dispensing into individual gel applicator or an applicator pad or felt tipped pad as those found on highlighter markers. The composition may be inconspicuous as by transparency, environmentally stable, and nontoxic, dry rapidly, be readily wetted by spray disinfectants, liquid disinfectants, or other cleaning agents, and be easily removed with light abrasion.

The composition includes a carrier, an optical brightener, and a complexing agent, as needed. In a preferred embodiment the composition further includes a surfactant, a solvent for quick drying, a preservative and a thickener.

U.S. Pat. No. 7,718,395 to Carling et al entitled "Monitoring Cleaning of Surfaces" discloses a transparent system for monitoring cleaning employing a source of adherence such as natural glue such as methyl cellulose or ethyl cellulose which comprises up to almost 50% of the composition. Such formulations are difficult to apply and remove from the surfaces due to the presence of the glue. Further current commercial formulations have been shown to cause a residual "ghost" mark on surfaces which are frequently cleaned with quaternary disinfectant cleaners. The compositions of the invention overcome these problems and disclose a stable composition that dries quickly with the use of solvent, is easily removed, is low foaming, and also has an improved viscosity.

In one embodiment the fluorescent gel formula comprises from about 0 to about 20 wt % surfactant, from about 0.001 to about 10 wt % cationic complexing agent, from about 0 to about 40 wt % solvent such as alcohol, from about 0.001 to about 5 wt % anionic optical brightener, from about 0 to about 0.5 wt % preservatives and from 0 to about 5 wt % thickener agent with any remainder being water.

In another embodiment the fluorescent gel formula comprises from about 0 to about 20 wt % surfactant, from about 0.001 to about 10 wt % anionic complexing agent, from about 0 to about 40 wt % solvent such as alcohol, from about 0.001 to about 5 wt % cationic optical brightener, from about 0 to about 0.5 wt % preservatives and from 0 to about 5 wt % thickener agent with any remainder being water.

In another embodiment the complexing agent may be omitted and the gel formula comprises from about 0 to about 20 wt % surfactant, from about 0 to about 40 wt % solvent such as alcohol, from about 0.001 to about 5 wt % cationic optical brightener, and from about 0 to about 0.5 wt % preservatives and from 0 to about 5 wt % thickener agent (preferably nonionic) with any remainder being water.

The complexing agent can be any compound with opposite charge to the optical brightener that will function to neutralize the charge of the brightener and impart the ability of the complex to be removed. This can include surfactants, modified celluloses, modified guar, modified acrylic compounds, modified urethane, PVP, and ethoxycarboxylates. Non-limiting examples of complexing agents include but are not limited to: alkylphenolethoxylate carboxylate (more specifically where the ethoxylate chain is greater than 5 EO units such as nonylphenolethoxylatesulfonate), alkyl ether phosphates, alkyl phenol ether phosphates, alkyl phenol ether sulphates, alkyl ether carboxylic acids and salts, alkyl ether sulphates, nonylphenol ethoxylated phosphate esters (preferably greater than POE-5), phosphate esters of an alkyl polyethoxyethanol (STEPFAC™ 8180, 8181, and 8182 from Stepan), ethoxylated alkyl amines such as ethoxylated coco amine, ethoxylated polyarylphenol sulfate ammonium salt, methacrylic acid/sodium acrylamidomethyl propane sulfonate copolymer, polyquaternium-1, polyquaternium-2, polyquaternium-3, polyquaternium-4, polyquaternium-5, polyquaternium-6, polyquaternium-7, polyquaternium-10, polyquaternium-11, polyquaternium-15, polyquaternium-16, polyquaternium-22, polyquaternium-28, polyquaternium-32, polyquaternium-37, polyquaternium-39, polyquaternium-46, polyquaternium-4, acrylamido-methyl-propane sulfonate polymer (AMPS), polystyrene sulfonate, poly-L-glutamate, polyacrylamide cationic copolymers, and polyacrylamide anionic copolymers. In many embodiments, the complexing agent may be a surfactant.

Surfactants

Surfactants may be used as an additional component of the composition, and/or may be the complexing agent in the formulation which serves to interact with the optical brightener. Examples of surfactants with maybe used include cationic, anionic, nonionic, or zwitterionic. In addition, cationic, or anionic surfactants may also be the complexing agent depending upon the charge of the optical brightener. In a preferred embodiment, when the surfactant is not functioning as a complexing agent, the surfactant is a nonionic surfactant.

Anionic surfactants/complexing agents that can be used according to the invention include any anionic surfactant available in the cleaning industry. Suitable groups of anionic surfactants include sulfonates and sulfates. Suitable surfactants that can be provided in the anionic surfactant component include alkyl aryl sulfonates, secondary alkane sulfonates, alkyl methyl ester sulfonates, alpha olefin sulfonates, alkyl ether sulfates, alkyl sulfates, and alcohol sulfates.

Suitable alkyl aryl sulfonates that can be used in the cleaning composition can have an alkyl group that contains 6 to 24 carbon atoms and the aryl group can be at least one of benzene, toluene, and xylene. A suitable alkyl aryl sulfonate includes linear alkyl benzene sulfonate. A suitable linear alkyl benzene sulfonate includes linear dodecyl benzyl sulfonate that can be provided as an acid that is neutralized to form the sulfonate. Additional suitable alkyl aryl sulfonates include xylene sulfonate and cumene sulfonate.

Suitable alkane sulfonates that can be used in the cleaning composition can have an alkane group having 6 to 24 carbon atoms. Suitable alkane sulfonates that can be used include secondary alkane sulfonates. A suitable secondary alkane sulfonate includes sodium $C_{14}$-$C_{17}$ secondary alkyl sulfonate commercially available as Hostapur SAS from Clariant.

Suitable alkyl methyl ester sulfonates that can be used in the cleaning composition include those having an alkyl group containing 6 to 24 carbon atoms. Suitable alpha olefin sulfonates that can be used in the cleaning composition include those having alpha olefin groups containing 6 to 24 carbon atoms.

Suitable alkyl ether sulfates that can be used in the cleaning composition include those having between about 1 and about 10 repeating alkoxy groups, between about 1 and about 5 repeating alkoxy groups. In general, the alkoxy group will contain between about 2 and about 4 carbon atoms. A suitable alkoxy group is ethoxy. A suitable alkyl ether sulfate is sodium lauryl ether sulfate and is available under the name Steol CS-460.

Suitable alkyl sulfates that can be used in the cleaning composition include those having an alkyl group containing 6 to 24 carbon atoms. Suitable alkyl sulfates include, but are not limited to, sodium lauryl sulfate and sodium lauryl/myristyl sulfate.

Suitable alcohol sulfates that can be used in the cleaning composition include those having an alcohol group containing about 6 to about 24 carbon atoms.

The anionic surfactant can be neutralized with an alkaline metal salt, an amine, or a mixture thereof. Suitable alkaline metal salts include sodium, potassium, and magnesium. Suitable amines include monoethanolamine, triethanolamine, and monoisopropanolamine. If a mixture of salts is used, a suitable mixture of alkaline metal salt can be sodium and magnesium, and the molar ratio of sodium to magnesium can be between about 3:1 and about 1:1.

The composition can contain a nonionic surfactant component. Nonionic surfactants that can be used in the composition include polyalkylene oxide surfactants (also known as polyoxyalkylene surfactants or polyalkylene glycol surfactants). Suitable polyalkylene oxide surfactants include polyoxypropylene surfactants and polyoxyethylene glycol surfactants. Suitable surfactants of this type are synthetic organic polyoxypropylene (PO)-polyoxyethylene (EO) block copolymers. These surfactants include a di-block polymer comprising an EO block and a PO block, a center block of polyoxypropylene units (PO), and having blocks of polyoxyethylene grafted onto the polyoxypropylene unit or a center block of EO with attached PO blocks. Further, this surfactant can have further blocks of either polyoxyethylene or polyoxypropylene in the molecules. A suitable average molecular weight range of useful surfactants can be about 1,000 to about 40,000 and the weight percent content of ethylene oxide can be about 10-80 wt %.

Additional nonionic surfactants include alcohol alkoxylates. An suitable alcohol alkoxylate include linear alcohol ethoxylates such as Tomadol™ 1-5 which is a surfactant containing an alkyl group having 11 carbon atoms and 5 moles of ethylene oxide. Additional alcohol alkoxylates include alkylphenol ethoxylates, branched alcohol ethoxylates, secondary alcohol ethoxylates (e.g., Tergitol 15-S-7 from Dow Chemical), castor oil ethoxylates, alkylamine ethoxylates, tallow amine ethoxylates, fatty acid ethoxylates, sorbital oleate ethoxylates, end-capped ethoxylates, or mixtures thereof. Additional nonionic surfactants include amides such as fatty alkanolamides, alkyldiethanolamides, coconut diethanolamide, lauric diethanolamide, polyethylene glycol cocoamide (e.g., PEG-6 cocoamide), oleic diethanolamide, or mixtures thereof. Additional suitable nonionic surfactants include polyalkoxylated aliphatic base, polyalkoxylated amide, glycol esters, glycerol esters, amine oxides, phosphate esters, alcohol phosphate, fatty triglycerides, fatty triglyceride esters, alkyl ether phosphate, alkyl esters, alkyl phenol ethoxylate phosphate esters, alkyl polysaccharides, block copolymers, alkyl polyglucosides, or mixtures thereof. An alcohol alkoxylate nonionic surfactant is a preferred surfactant.

Amphoteric surfactants can also be used and include, but are not limited to: betaines, imidazolines, and propionates. Suitable amphoteric surfactants include, but are not limited to: sultaines, amphopropionates, amphodipropionates, aminopropionates, aminodipropionates, amphoacetates, amphodiacetates, and amphohydroxypropylsulfonates.

Cationic surfactants/complexing agents that can be used include, but are not limited to: amines such as primary, secondary and tertiary monoamines with $C_{18}$ alkyl or alkenyl chains, ethoxylated alkylamines, alkoxylates of ethylenediamine, imidazoles such as a 1-(2-hydroxyethyl)-2-imidazoline, a 2-alkyl-1-(2-hydroxyethyl)-2-imidazoline, and the like; and poly phosphate ammonium salts, as for example, alkylpoly phosphate ammonium chloride surfactants such as n-alkyl($C_{12}$-$C_{18}$)dimethylbenzyl ammonium chloride, n-tetradecyldimethylbenzylammonium chloride monohydrate, and a naphthylene-substituted poly phosphate ammonium chloride such as dimethyl-1-naphthylmethylammonium chloride.

Preferred cationic surfactants/complexing agents include dialkylamido ethyl hydroxyethylmonium salt, dialkylamidoethyl dimonium salt, dialkyloyl ethyl hydroxyethylmonium salt, dialkyloyl ethyldimonium salt, and mixtures thereof; for example, commercially available under the following tradenames; VARISOFT 110, VARISOFT 222, VARIQUAT K1215 and VARIQUAT 638 from Witco Chemicals, MACKPRO KLP, MACKPRO WLW, MACKPRO MLP, MACKPRO NSP, MACKPRO NLW, MACKPRO WWP, MACKPRO NLP, MACKPRO SLP from McIntyre, ETHOQUAD 18/25, ETHOQUAD O/12PG, ETHOQUAD C/25, ETHOQUAD S/25, and ETHODUOQUAD from Akzo, DEHYQUAT SP from Henkel, and ATLAS G265 from ICI Americas.

Suitable solvents useful for the present invention include water and other solvents such as lipophilic fluids including alcohol to help the composition to dissolve and evaporate quickly. Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof. In some embodiments, the solvent includes water. The water can include water from any source including deionized water, tap water, softened water, and combinations thereof.

The viscosity of the composition increases with the amount of thickening agent, and viscous compositions are useful for uses where composition clings to the surface. Suitable thickeners can include those which do not leave contaminating residue on the surface to be treated. Generally, thickeners which may be used in the present invention include natural gums such as xanthan gum, guar gum, modified guar, or other gums from plant mucilage; polysaccharide based thickeners, such as alginates, starches, and cellulosic polymers (e.g., carboxymethyl cellulose, hydroxyethyl cellulose, and the like); polyacrylates thickeners; and hydrocolloid thickeners, such as pectin. In some embodiments without a cationic compound, the preferred thickener is a nonionic thickener such as cellulosic polymers mentioned supra.

Optical brighteners are a specific class of fluorophores that absorb UV light (200-400 nm) and emit blue light in the visible spectrum. Fluorophores are molecules that absorb light of higher energy and emit light of lower energy, and may contain excitation and emission spectra throughout the UV and visible regions. Examples of optical brighteners are molecules that include, but are not limited to, derivatives of stilbene, biphenyl, naphthalene and anthracene. Exemplary molecules may be found in the Kirk-Othmer Encyclopedia of Chemical Technology. Examples of fluorophores include, but are not limited to, fluorescein, rhodamine, Cy5 and their derivatives. When the optical agent is a food dye, textile dye or D&C dye, the absorbance is in the visible region (400-800 nm). Exemplary molecules may be found in the FD&C Handbook and are chosen accordingly by their chemical and spectral properties by a person skilled in the art.

An optical brightener is included which fluoresces under UV light and is the indicator of the presence of the composition after cleaning. Optical brighteners useful in the present invention are known and commercially available. Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles and other miscellaneous agents. Examples of these types of brighteners are disclosed in "The Production and Application of Fluorescent Brightening Agents", M. Zahradnik, Published by John Wiley & Sons, New York (1982), the disclosure of which is incorporated herein by reference.

Stilbene derivatives which may be useful in the present invention include, but are not necessarily limited to, derivatives of bis(triazinyl)amino-stilbene; bisacylamino derivatives of stilbene; triazole derivatives of stilbene; oxadiazole derivatives of stilbene; oxazole derivatives of stilbene; and styryl derivatives of stilbene. In an embodiment, optical brighteners include stilbene derivatives. In some embodiments, the optical brightener includes Tinopal UNPA, which is commercially available through the Ciba Geigy Corporation located in Switzerland.

Additional optical brighteners for use in the present invention include, but are not limited to, the classes of substance of 4,4'-diamino-2,2'-stilbenedisulfonic acids (flavonic acids), 4,4'-distyrylbiphenyls, methylumbelliferones, coumarins, dihydroquinolinones, 1,3-diarylpyrazolines, naphthalimides, benzoxazol, benzisoxazol and benzimidazol systems, and pyrene derivatives substituted by heterocycles, and the like. Optical brighteners are disclosed in WO1999013833 entitled "Hair Care Compositions Comprising Optical Brighteners and Cationic Compounds", the disclosure of which is hereby incorporated by reference. In a preferred embodiment the optical brightner is a stilbene derivative.

The optical brightener may be anionic or cationic. Commercially available examples of suitable cationic optical brightening agents are Blankophor™ ACR (Bayer) and Leucophor™ FTS (Clariant). Anionic optical brighteners are described e.g. in U.S. Pat. No. 4,888,128. Commercially available examples of anionic optical brighteners include a hexasulfonated stilbene derivative, which is available from Ciba Specialty Chemical Corp., 540 White Plains Road, Tarrytown, N.Y. 10591 ("Ciba Specialty"), under the product designation TINOPAL ABP.

Preservatives are optional and are generally preferred when the formula pH is not high enough to mitigate bacterial growth. Examples of preservatives useful in compositions of the invention include but are not limited to methyl paraben, glutaraldehyde, formaldehyde, 2-bromo-2-nitropropane-1,3-diol, 5-chloro-2-methyl-4-isothiazoline-3-one, and 2-methyl-4-isothiazoline-3-one.

Examples of commercial sources of suitable components are as follows in Table 1:

TABLE 1

| Composition | Description | Trade name | supplier |
| --- | --- | --- | --- |
| Surfactant | Alcohol alkoxylate | Lutensol XP 80 | BASF |
| Surfactant | Alcohol alkoxylate | Tomadol 91-6 | Air Products |
| Surfactant | Amphoteric Surfactant | Tomamine Amphoteric 400 | Air Products |
| Complexing surfactant | Cationic compound | Variquat K1215 | Witco |

TABLE 1-continued

| Composition | Description | Trade name | supplier |
|---|---|---|---|
| Dye/Optical rightener | Stilbene derivative | D-282 | Day Glo |
| | | Leucophor FTS liq. | Clariant |
| Alcohol | Isopropyl alcohol | IPA | Brenntag |
| Thickener agent | Xanthan gum | Clarified Xanthan Gum Kelzan T | Kelco |
| | hydroxyethylcellulose | Natrosol 250H4BR | Herceles |
| Preservative | Chloro methyl isothiazolin | Kathon CG/ICP II | Rohm and Haas/Dow |
| | phenoxyethanol | Phenoxetol | Clariant |
| Water | Water | | |

Examples of formulations according to the invention are below in Table 2:

TABLE 2

| Composition | Description/example | Weight % First range | Weight % Second range | Weight % Third range |
|---|---|---|---|---|
| Surfactant | Alcohol alkoxylate/amphoteric surfactant | 0-20 | 0-18 | 0-15 |
| Cationic/anionic complexing agent | Cationic/anionic Compound (depending upon optical brightener) | 0.001-10 | 0.01-7 | 0.1-5 |
| Dye/Optical brightener (cationic or anionic) | Cationic/anionic | 0.001-5 | 0.005-4 | 0.01-3 |
| solvent | alcohol | 0-40 | 0-20 | 0-10 |
| Thickener agent | Xanthan gum | 0-5 | 0-2.5 | 0-1 |
| Preservative | Chloro methyl isothiazolin | 0-.5 | 0-0.01 | 0-0.001 |
| Water | Water | 40-95 | 45-90 | 50-85 |

Examples of formulations without a cationic compound are below in Table 3:

TABLE 3

| Composition | Description/example | Weight % First range | Weight % Second range | Weight % Third range |
|---|---|---|---|---|
| Surfactant | Alcohol alkoxylate | 0-20 | 0-10 | 0-5 |
| Dye/Optical brightener | stilbene derivative (cationic) | 0.001-10 | 0.01-7 | 0.1-4 |
| solvent | Isopropyl alcohol | 0-40 | 0-20 | 0-10 |
| Thickener agent | hydroxy-ethylcellulose | 0-5 | 0-3 | 0-2 |
| Preservative | Chloro methyl isothiazolin | 0-.5 | 0-0.01 | 0-0.001 |
| Water | Water | 50-99 | 60-97 | 70-95 |

The formula also can be made without or much less of thickener in order to pack into an applicator more or less like a highlighter pen with a filter and a felt tip. A solid composition is also possible.

Methods Employing the Compositions of the Invention

Prior to cleaning of a room, the composition or targeting solution may be deposited on targets such as those indicated herein and fixed to the surface, as, for example, by being allowed to dry. Since the dried composition does not occupy a location likely to encounter abrasion from daily activities, its removal may be assumed to be the result of cleaning activities. When the dried targeting solution is transparent, those engaged in cleaning activities are unaware of target locations. Consequently, they are not biased to clean areas adjacent to the targets and to avoid non-adjacent areas.

After a single cleaning opportunity or multiple cleaning opportunities are presented, cleaning activities may be suspended. That is, further cleaning in the room may not be permitted until the target areas are scanned. The targets within a room may be then scanned with a device able to render visible the dried composition so as to reveal the extent to which the targets have been subjected to cleaning. A target may be considered to have been cleaned if the dried composition was removed or clearly disturbed. If the composition contains a material fluorescent under exposure to ultraviolet radiation, a UV source may be held over the target locations to reveal dried composition not removed during cleaning The compositions of the invention have several advantages over other commercially available formulas. The presently disclosed compositions form a stable formulation which has a viscosity suitable for application through a foam applicator pad or felt tipped pad as those found on highlighter markers. Other prior formulas have a viscosity which was too high for this type of application and resulted in a thick glob when dabbed onto a surface. This glob dried to a rough sticky solid clearly visible where applied. The current formulation also has a viscosity suitable for dispensing into individual gel applicator. Applicants' formulations are also low foaming and quick drying to the surface and do not leave any rough or sticky residue.

When the formulations of the invention are applied to the surface and allowed to dry, they are easy to remove by standard cleaning and can be removed without scrubbing. The formulations also inhibit the formation of an insoluble complex between the anionic optical brightener and residual surface cationic quaternary based surfactants which leave behind a faint image of the surface mark when wiped using normal cleaning procedures. In addition, cationic optical brighteners and anionic complexing agents would inhibit the formation of an insoluble complex on surfaces where a negative charge would remain. Hard surfaces can be negatively charged whether they have not been treated or have been treated with cleaning compositions which leave residue that contains an overall negative charge.

Methods of Making the Compositions of the Invention

The formulations of the invention may be made by conventional techniques. The thickener and water are preferably blended together first while stirring to allow the solution to thicken. Stirring may take up to 30 minutes to complete the process and for the solution to achieve the desired consistency. The solution may also be heated to approximately 50° C. to aid in the process. Other components are then simply added while stirring.

The composition may then be further processed as desired and as known in the art for creating various gel thicknesses or even solids.

EXAMPLE 1

A formulation according to the invention was prepared as follows in Table 4:

TABLE 4

| Composition | Description | Weight % |
|---|---|---|
| Complexing agent | Cationic Compound | .5 |
| Dye/Optical Brightener | stilbene derivative (anionic) | 3 |
| Alcohol | Isopropyl alcohol | 5 |
| Thickener agent | Xanthan gum | .9 |
| Preservative | Chloro methyl isothiazolin | 1 |
| Water | Water | remainder |

Surface Residual Test:

Prepare one liter of a 1 to 64 dilution of quaternary disinfectant cleaner commercially available from Ecolab, Inc. in 5 grain water. Add three Polifix micro fiber cloths commercially available from Ecolab, Inc. to the liter of solution. Gently ring out the first micro fiber cloth to remove excess water and then wipe the cloth over the testing surface leaving a liquid film on the surface. Allow the liquid to dry. Repeat the application and drying on the surface a minimum of five times. To increase the severity of the test, continue quaternary disinfectant solution application to the surface. Surfaces for testing include Formica, melamine, stainless steel, epoxy resin, and ABS plastic. Using a cotton swab or foam applicator, apply a one inch diameter circle of the test marking solution to the surface. Allow the marking solution to dry. Using a black light source, check the glow of the dye on the surface. Decreasing the ambient light in the testing location will increase the relative brightness of the mark as will increasing the intensity of the black light source. Using a second micro fiber cloth from the initial solution, wipe the micro fiber cloth over the surface containing the mark. Again using a black light source check the glow of the dye after cleaning. Before cleaning it should have enough fluorescent glowing under black light to be visible under normal lighting conditions. A regular cleaning process should clean the applied area relatively easy. After cleaning lights should be dimmed as low as possible and there should be no residual dye in the form of a "ghost" mark (faint residual image in the shape of the initial mark on the surface). All the performance testing is completed by visual comparison.

The formulation was used in a Surface Residual Test as described above and applied to a hospital room and compared to a commercially available treatment formulation as a control. The results are below in Table 5:

TABLE 5

| | Cleaned 24 hours prior | | Cleaned just before | |
|---|---|---|---|---|
| Surface | Formulation of invention | CONTROL | Formulation of Invention | CONTROL |
| Bedroom vanity | No mark | mark | No mark | mark |
| faucet | No mark | mark | No mark | No mark |
| Towel dispenser | No mark | mark | No mark | mark |
| Overbed table | No mark | Light mark | Light mark | mark |
| Doorknob | No mark | mark | No mark | mark |
| Bathroom vanity | No mark | mark | No mark | mark |
| Bathroom light switch | No mark | mark | Light mark | mark |
| bathtub | No mark | No mark | No mark | No mark |
| Bathtub chair | Light mark | mark | Very light mark | mark |
| toilet | No mark | mark | No mark | mark |
| Bath grab bar | No mark | Very light mark | Very light mark | mark |
| Formica countertop | No mark | mark | Light mark | mark |
| Wooden chair arms | No mark | mark | Light mark | mark |
| Bed side rail | No mark | No mark | No mark | No mark |
| Bed end rail | No mark | Light mark | Light mark | mark |
| Black chair arms | No mark | mark | No mark | mark |
| nightstand | No mark | mark | Light mark | mark |
| phone | No mark | Very light mark | Light mark | mark |
| Call button | No mark | No mark | No mark | No mark |
| Sharps container | No mark | mark | Very light mark | mark |
| Linen top (stainless) | No mark | No mark | N/A | N/A |
| Window sill | No mark | mark | mark | mark |
| Corner rail (textured) | No mark | No mark | Light mark | mark |
| Wooden closet door | No mark | mark | No mark | mark |

As can be seen the formulations of the invention demonstrate a significant improvement over the control in the ability to be removed from the surface after drying without leaving a residue or mark.

EXAMPLE 2

Examples of formulations without a cationic compound are below in Table 6:

TABLE 6

| Composition | Description | Weight % |
|---|---|---|
| Surfactant | Alcohol alkoxylate | 0.01-5 |
| Dye/Optical brightener | stilbene derivative (cationic) | 0.1-4 |
| Alcohol | Isopropyl alcohol | 0.1-10 |
| Thickener agent | Hydroxyethylcellulose (nonionic) | 0-2 |
| Preservative | Chloro methyl isothiazolin | 0.1-0.25 |
| Water | Water | 70-95 |

A surface residual test was run as described in Example 1, the results are below in Table 7.

TABLE 7

| Surface | Formulation of invention (no cationic compound) | CONTROL |
|---|---|---|
| Overbed table | No mark | mark |
| nightstand | No mark | Light mark |
| phone | No mark | mark |
| Side rail of bed | No mark | No mark |
| Formica countertop | No mark | mark |
| Light switch | No mark | No mark |
| Toilet seat | No mark | No mark |
| Toilet grab bar | No mark | No mark |
| faucet | No mark | No mark |
| Bathroom vanity | No mark | Light mark |
| Linen cart | Very very light mark | mark |
| Wood closet door | No mark | No mark |
| Black armchair (textured) | Very light mark | mark |
| Room vanity | No mark | No mark |
| tub | No mark | No mark |
| Sharps container | No mark | mark |
| Shower seat | Very light mark | mark |
| Foot rail of bed | No mark | No mark |
| Wood armchair | No mark | mark |

As can be seen, the formulation without the cationic compound gave superior removal from surfaces when compared to the commercially available control. Only a very light or no mark was left on high gloss surfaces. As can be seen the formulations of the invention demonstrate a significant improvement over the control in the ability to be removed from the surface after drying without leaving a residue or mark.

EXAMPLE 3

Material Compatibility Test

An experiment was conducted to complete a large scale test of materials that are used to construct the high touch surface objects. Test the material substrates for compatibility using six different disinfectants at their suggested usage level. The disinfectants were applied using microfiber towels. Two different predetermined numbers of applications were performed where three different formulations of the invention applied and washed then observed for residual using multiple UV blacklights.

TABLE 8

| Materials tested | | |
|---|---|---|
| | Representative High Touch Surface | Other surfaces in hospital room |
| Laminate countertop | Over bed table | |
| Shiny nickel | Bathroom door handle | Bathroom fixtures |
| Zinc plated | Toilet handle | Door push plate |
| Engravers brass | Bathroom door handle | |
| 50% ABS (black) | Call button, telephone | |
| 75% ABS (black) | Call button, telephone | |
| Marble | | Vanity |
| Black ceramic tile | | Bathroom walls, tub |
| White ceramic tile | | Bathroom walls, tub |
| Granite | | Vanity |
| White textured ABS | Call button, telephone | |
| Aluminum | Bed rail | |
| Polystyrene | Toilet seat | |
| Polypropylene | Bed rail | |
| Brushed nickel | Bathroom door handle | Bathroom fixtures |
| Laminate | Over bed table | Vanity |
| Stainless steel | Toilet grab bar | |

Disinfectants:

| Name | Active |
|---|---|
| Quat Disinfectant Cleaner | ADBAC/DDAC |
| Oxivir | LAS/Peroxide |
| Peroxyacetic acid | peroxide/peracetic acid |
| Bleach wipes | chlorine bleach |
| Beaucoup | phenolic |
| Virasept | octanoic/peroxide/peracid |

UV Lights:
UV LED keychain lights×5
5.5" black light
11" black light
Stylus LED Flashlight (365 nm)
DSE custom light (395 nm at constant output)
Source of Light for Observing Marks:
Completely dark with no light allowed
Darkness with only day light allowed (lab F6310)
Full fluorescent lights in room without any daylight
Fluorescent Indicators:
First generation Representative Composition of the invention D1
Second generation Representative Composition of the invention D2
Hard Surface Representative composition of the invention H
Procedure:
1. Prepare six sets of tiles by placing the material coupons similar to the placement above. Attach coupons by using adhesive.
2. Prepare disinfectant cleaning solutions per the label instructions for standard dilutions. Change fresh solution daily. For Bleach wipes, use fresh wipe for each application.

| Product | Dilution | for 500 g dilution |
|---|---|---|
| Quat Disinfectant Cleaner | 1.2 oz per gallon | 4.69 g/500 g |
| Oxavir | 8 oz per gallon | 31.25 g/500 g |
| Bleach wipes | RTU | as it/1wipe per tile |
| Beaucoup | 2 oz per gallon | 7.81 g/500 g |
| Virasept | RTU | as it is |
| 5 grain tap water | RTU | as it is |
| Peroxyacetic acid formula | 3 oz/gal | 11.73 g/500 g |

3. Submerge 1 microfiber clothes into 500 g of the disinfectant solutions and let ut saturate. Lightly squeeze out excess solution and use that wet microfiber cloth to wet the complete surface of the material coupons on the tile. Test application is about 6 times per day/5 days period (total 30 applications).
4. Apply fluorescent marks of each formula using a foam applicator. Remain consistent on how the order of the marks.
5. Using each solution, clean the surface of the tiles as previously by saturating the surface and wiping.
6. Under the three different light conditions, observe the amount of removal of the fluorescent indicators. If residual marks remain, rate the intensity of the marks. Observe the presence of marks using all different UV lights.

Rating System

The tiles are observed under the specified lighting conditions using the different UV light sources. The rating was limited to one judge due to the time requirement of reading all the tiles. The tiles were read in random order and UV lights were used in random order. All tiles were read twice to confirm original judging. The rating was based on a scale of 0-5. The rating of 0 was given when there was absolutely no visible ghosting from any angle. A very faint mark was given a rating of 1 and was usually given when only a partial circular mark was apparent. This may also have been very faint in appearance, even to the experienced grader. Ratings of 2-5 were based on intensity of fluorescence. Occasionally, there would not be a full circular mark with the higher ratings but the UV intensity would still be intense.

Fluorescent Marking Gel formulas

TABLE 9

Representative Composition of the Invention D1 (Anionic optical brightener and no complexing agent)

| Quantity | Description |
|---|---|
| 92.60 | Water DI |
| 1.50 | Distyryl Biphenyl Derivative BAG |
| 0.30 | Alcohol Alkoxylate, C10 |
| 0.15 | Chloro Methyl Isothiazolin mixture DRM |
| 5.00 | Isopropyl Alcohol 99% DRM |
| 0.45 | Xanthan Gum |

TABLE 10

Representative Composition of the Invention D2 (Anionic optical brightener with complexing agent)

| Quantity | Description |
|---|---|
| 73.65 | Water DI |
| 1.00 | C.I. Fluorescent Brightener 220 BAG |
| 0.35 | Xanthan Gum |
| 4.00 | Linear Alcohol Ethox (C9-C11) 6 EO DRM |
| 1.00 | Alcohol Alkoxylate, C10 |

TABLE 10-continued

Representative Composition of the Invention D2 (Anionic optical brightener with complexing agent)

| Quantity | Description |
|---|---|
| 12.00 | disodium Octylimino dipropionate 50% |
| 2.00 | PEG 15 cocomonium chlor; |
| 1.00 | Phenoxyethanol DRM |
| 5.00 | Isopropyl Alcohol 99% DRM |

TABLE 11

Representative Composition of the Invention H (Cationic optical brightener and no complexing agent)

| Quantity | Description |
|---|---|
| 90.45 | Water DI |
| 0.90 | Natrosol 250H4BR |
| 3.00 | Leucophor FTS liq. |
| 0.50 | Lutensol XP80 |
| 0.15 | Kathon CG/ICP II (1.5% active) |
| 5.00 | IPA |

Results

The data shown in charts 1 to 7 is only a small portion of the total data that was generated. This particular data was chosen as the worst conditions to observe ghost marks.

Quat Disinfectant Cleaner (ADBAC/DDAC)

CHART 1

For the test with Quat Disinfectant Cleaner, the following are the results for ghost marks showing in complete darkness using the Stylus UV flashlight and the Large Fluorescent Lamp.

| | | D1 | D2 | H | D1 | D2 | H |
|---|---|---|---|---|---|---|---|
| | | | Quat Disinfectant Cleaner | | | Quat Disinfectant Cleaner | |
| Laminate countertop | Stylus UV flashlight (pen light) | | | | Large fluorescent | | |
| Shiny nickel zinc plated | | 2 | | | 2 | | |
| Engravers Brass | | 1 | 1 | | 1 | 1 | |
| 50% ABS | | | 1 | | | 2 | |
| 75% ABS | | | 1 | | | 2 | |
| marble | | 1 | 5 | 5 | 1 | 5 | 5 |
| granite | | | 1 | 1 | | 1 | 1 |
| black ceramic tile | | | | | | | |
| white ceramic tile | | | | | | | |
| ABS textured | | | 1 | | | 1 | |
| Aluminum | | 3 | 1 | 1 | 3 | | |
| Polystyrene | | | 2 | | | 2 | |
| polypropylene laminate | | | | | | | |
| Stainless Steel | | 1 | | | | | |
| Brushed Nickel | | | 2 | | | 2 | |
| Total # of marks on all (17) | | 5 | 9 | 3 | 4 | 8 | 2 |
| Total # of marks on nonporous (13) | | 4 | 7 | 1 | 3 | 6 | 0 |
| Sum on nonporous | | 7 | 9 | 1 | 6 | 10 | 0 |
| Total # of marks on metals (6) | | 4 | 3 | 1 | 3 | 1 | 0 |
| Total # of marks on hard surfaces (7) | | 0 | 4 | 0 | 0 | 4 | 0 |

This was the best cleaner for formula H and the marks that showed up were only on metal coupons. The cationic optical brightener and the charge left on the surfaces are compatible, therefore not causing complexing.

This was the worst cleaner for formula D1 and interacting on all surfaces. This is reflective of the problem that was seen with traditional products. The anionic optical brightener is interacting with the quat that is being left on the surface and causing a strong complex to form. Generally this complex is difficult to remove. Note: this performed similar to Virasept.

This was the best cleaner for formula D2 for all hard surfaces and most metals. The coupling of the anionic brightener and a quat surfactant eliminates the interaction that would be caused when coming in contact with the positively charged quat residual on the surfaces.

Water (No Cleaner)

CHART 2

For the test with only water as a cleaner, the following are the results for ghost marks showing in complete darkness using the Stylus UV flashlight and the Large Fluorescent Lamp.

|  |  | D1 | D2 | H |  | D1 | D2 | H |
|---|---|---|---|---|---|---|---|---|
|  |  | Tap water |  |  |  | Tap water |  |  |
| Laminate countertop | Pen light | 2 |  |  | Large fluorescent | 2 | 1 | 1 |
| Shiny nickel |  | 1 |  |  |  | 1 |  |  |
| zinc plated |  | 3 |  |  |  | 3 |  |  |
| Engravers Brass |  | 1 |  |  |  | 1 |  |  |
| 50% ABS |  | 1 |  |  |  | 1 |  |  |
| 75% ABS |  | 1 |  |  |  | 1 |  |  |
| marble |  | 3 | 5 | 5 |  | 3 | 5 | 5 |
| granite |  | 3 | 2 | 2 |  | 2 | 1 | 1 |
| black ceramic tile |  |  |  |  |  |  |  |  |
| white ceramic tile |  |  |  |  |  |  |  |  |
| ABS textured |  | 2 | 1 |  |  | 2 | 2 |  |
| Aluminum |  | 4 |  |  |  | 4 | 1 | 1 |
| Polystyrene |  |  |  |  |  | 1 | 1 |  |
| polypropylene laminate |  | 4 |  |  |  | 3 |  |  |
| Stainless Steel |  | 4 |  |  |  | 3 |  |  |
| Brushed Nickel |  | 5 |  |  |  | 4 |  |  |
| Total # of marks on all (17) |  | 13 | 3 | 2 |  | 14 | 6 | 4 |
| Total # of marks on nonporous (13) |  | 11 | 1 | 0 |  | 12 | 4 | 2 |
| Sum on nonporous |  | 28 | 1 | 0 |  | 26 | 5 | 2 |
| Total # of marks on metals (6) |  | 6 | 0 | 0 |  | 6 | 1 | 1 |
| Total # of marks on hard surfaces (7) |  | 5 | 1 | 0 |  | 6 | 3 | 1 |

This was tied as the worst cleaner for formula H, Ghosting occurred on both metals and hard surfaces. Laminate was the worst hard surface. Generally, hard surfaces have negative charges on them when they haven't been treated with anything. The cationic optical brightener in this formula formed a bond with the negative ions on the surfaces and caused ghosting. This supports the theory that pre-complexing the cationic optical brightener with an anionic surfactant would be useful.

This was the best cleaner for formula D1 with marks occurring very light on ABS and polystyrene. The negative ions on the untreated surface would not interact with the anionic optical brightener and there shouldn't be any ghost marks, with the exception of porous surfaces.

The results for D1 are similar to D2 but there was still a very light mark on laminate.

Virasept (Octanoic/Peroxide/Peracid)

CHART 3

For the test with Virasept, the following are the results for ghost marks showing in complete darkness using the Stylus UV flashlight and the Large Fluorescent Lamp.

|  |  | D1 | D2 | H |  | D1 | D2 | H |
|---|---|---|---|---|---|---|---|---|
|  |  | Virasept |  |  |  | Virasept |  |  |
| Laminate countertop | Pen light | 1 | 2 | 1 | Large fluorescent | 1 | 3 | 1 |
| Shiny nickel |  |  |  |  |  |  |  |  |
| zinc plated |  | 1 |  |  |  | 2 |  |  |
| Engravers Brass |  |  |  |  |  |  |  |  |
| 50% ABS |  | 1 |  |  |  | 1 |  |  |
| 75% ABS |  | 2 | 1 |  |  | 1 |  |  |
| marble |  | 3 | 5 | 5 |  | 3 | 5 | 5 |
| granite |  |  |  |  |  | 2 | 1 | 1 |
| black ceramic tile |  |  |  |  |  |  |  |  |
| white ceramic tile |  |  |  |  |  |  |  |  |
| ABS textured |  | 1 | 2 |  |  | 2 | 3 | 1 |
| Aluminum |  |  |  |  |  | 1 |  |  |
| Polystyrene |  | 2 | 3 | 1 |  | 2 | 3 | 1 |
| polypropylene laminate |  |  | 1 | 1 |  | 1 | 2 | 1 |
| Stainless Steel |  | 3 |  |  |  | 1 |  |  |
| Brushed Nickel |  | 3 |  |  |  | 2 |  |  |
| Total # of marks on all (17) |  | 9 | 6 | 4 |  | 12 | 6 | 6 |
| Total # of marks on nonporous (13) |  | 8 | 5 | 3 |  | 10 | 4 | 4 |
| Sum on nonporous |  | 14 | 9 | 3 |  | 14 | 11 | 4 |
| Total # of marks on metals (6) |  | 3 | 0 | 0 |  | 4 | 0 | 0 |
| Total # of marks on hard surfaces (7) |  | 5 | 5 | 3 |  | 6 | 4 | 4 |

There was a high level of ghosting with formula H, but the marks were relatively light for metal and hard surfaces. The negative charge remaining on the surface would probably have interacted with the cationic optical brightener in this formula. Since both metal and hard surfaces were ghosting, it is likely this was a charge interaction.

Similar to the Quat Disinfectant Cleaner, this was the worst for ghosting for formula D1. The interactions occurred only on hard surfaces and not metal. Polystyrene had a particularly strong interaction but laminate and ABS had lighter ghost marks. Since the ghosting only occurred on the hard surface materials, this might not be a surface charge interaction. Also, anything remaining as residual of this formula would have a negative charge, if any.

This was the worst cleaner for formula D2 as well. The interactions were much lighter than formula D1 but still showed up on polystyrene and laminate.

Beaucoup (Phenolic)

CHART 4

For the test with Beaucoup, the following are the results for ghost marks showing in complete darkness using the Stylus UV flashlight and the Large Fluorescent Lamp

|  |  | D1 | D2 | H |  | D1 | D2 | H |
|---|---|---|---|---|---|---|---|---|
|  |  | Beaucoup |  |  |  | Beaucoup |  |  |
| Laminate countertop | Pen light | 2 |  |  | Large fluorescent | 2 |  |  |
| Shiny nickel |  | 1 |  |  |  | 1 |  |  |

CHART 4-continued

For the test with Beaucoup,
the following are the results for ghost marks
showing in complete darkness
using the Stylus UV flashlight
and the Large Fluorescent Lamp

| | D1 | D2 | H | D1 | D2 | H |
|---|---|---|---|---|---|---|
| | Beaucoup | | | Beaucoup | | |
| zinc plated Engravers Brass | 1 | | cent | 1 | | |
| 50% ABS | 1 | | | 2 | | |
| 75% ABS | 2 | | | 2 | | |
| marble | 3 | 5 | 5 | 3 | 5 | 5 |
| granite | 1 | 2 | 2 | 1 | 2 | 1 |
| black ceramic tile | | | | | | |
| white ceramic tile | | | | | | |
| ABS textured | 1 | 2 | | 2 | 3 | |
| Aluminum | 3 | 1 | 1 | 2 | 1 | 1 |
| Polystyrene | 3 | 2 | | 2 | 2 | |
| polypropylene | | | | | | |
| laminate | 4 | | | 4 | | |
| Stainless Steel | 4 | | | 4 | | |
| Brushed Nickel | 4 | | | 4 | | |
| Total # of marks on all (17) | 13 | 5 | 3 | 14 | 5 | 3 |
| Total # of marks on nonporous (13) | 11 | 3 | 1 | 12 | 3 | 1 |
| Sum on nonporous | 26 | 5 | 1 | 27 | 6 | 1 |
| Total # of marks on metals (6) | 5 | 1 | 1 | 6 | 1 | 1 |
| Total # of marks on hard surfaces (7) | 6 | 2 | 0 | 6 | 2 | 0 |

This was tied as the worst cleaner for formula H, very similar to how it reacted with water. Ghosting occurred on both metals and hard surfaces. Laminate and polystyrene were difficult surfaces and ABS was less difficult. Since the active ingredient in Beaucoup is a phenol, there would be a negative residual charge on the surface. The cationic optical brightener in this formula probably forms a bond with the negative ions on the surfaces and caused the ghost marks. This supports the theory that pre-complexing the cationic optical brightener with an anionic surfactant would be useful.

Both formulas D1 and D2 performed well with this cleaner, which is expected as they both contain the anionic optical brightener. Formula D1 had light interactions on ABS and polystyrene, where formula D2 only had ghosting on metal surfaces.

Oxivir (LAS/Peroxide)

CHART 5

For the test with Oxivir,
the following are the results
for ghost marks showing
in complete darkness using the
Stylus UV flashlight and the Large Fluorescent Lamp.

| | | D1 | D2 | H | D1 | D2 | H |
|---|---|---|---|---|---|---|---|
| | | Oxivir | | | Oxivir | | |
| Laminate countertop | Pen light | 2 | 4 | 3 | Large fluo-res-cent | 2 | 5 | 4 |
| Shiny nickel | | | | | | | | |
| zinc plated | | 3 | | | | 3 | | |
| Engravers Brass | | | | | | | | |
| 50% ABS | | 1 | | | | 2 | | |
| 75% ABS | | 2 | | | | 3 | | |
| marble | | 2 | 4 | 4 | | 3 | 5 | 5 |

CHART 5-continued

For the test with Oxivir,
the following are the results
for ghost marks showing
in complete darkness using the
Stylus UV flashlight and the Large Fluorescent Lamp.

| | D1 | D2 | H | D1 | D2 | H |
|---|---|---|---|---|---|---|
| | Oxivir | | | Oxivir | | |
| granite | 2 | 1 | 1 | 2 | 1 | 1 |
| black ceramic tile | | | | | | |
| white ceramic tile | | | | | | |
| ABS textured | | | | 1 | 2 | |
| Aluminum | | | | | | |
| Polystyrene | 1 | | | 1 | 2 | |
| polypropylene | | | | | | |
| laminate | 2 | 4 | 3 | 2 | 4 | 2 |
| Stainless Steel | | | | | | |
| Brushed Nickel | 1 | | | 1 | | |
| Total # of marks on all (17) | 8 | 5 | 4 | 10 | 6 | 4 |
| Total # of marks on nonporous (13) | 6 | 3 | 2 | 8 | 4 | 2 |
| Sum on nonporous | 11 | 9 | 6 | 15 | 13 | 6 |
| Total # of marks on metals (6) | 2 | 0 | 0 | 2 | 0 | 0 |
| Total # of marks on hard surfaces (7) | 4 | 3 | 2 | 6 | 4 | 2 |

Formula H performed relatively mediocre with this cleaner. Mostly the ghosting was found on the hard surfaces. Two of the surfaces to note are laminate and ABS.

For formulas D1 and D2 there were very few marks but they were strong, especially on laminate. Since there were no marks on the metals with this cleaner, it may be a situation of how the cleaner physically affects the hard surfaces.

Bleach Wipes (Chlorine Bleach)

CHART 6

For the test with bleach wipes,
the following are the results for ghost marks
showing in complete
darkness using the Stylus UV
flashlight and the Large Fluorescent Lamp.

| | | D1 | D2 | H | | D1 | D2 | H |
|---|---|---|---|---|---|---|---|---|
| | | Bleach wipes | | | | Bleach wipes | | |
| Laminate countertop | Pen light | 2 | 1 | 1 | Large fluo-res-cent | 2 | 1 | 1 |
| Shiny nickel | | | | | | | | |
| zinc plated | | 1 | | | | 1 | | |
| Engravers Brass | | | | | | | | |
| 50% ABS | | | | | | | | |
| 75% ABS | | 1 | | | | | | |
| marble | | 3 | 5 | 5 | | 3 | 5 | 5 |
| granite | | | 1 | | | | 1 | |
| black ceramic tile | | | | | | | | |
| white ceramic tile | | | | | | | | |
| ABS textured | | | 1 | | | 1 | 2 | |
| Aluminum | | 3 | | | | 3 | | |
| Polystyrene | | 1 | 2 | | | 1 | 2 | |
| polypropylene | | | | | | | | |
| laminate | | 3 | | | | 3 | | |
| Stainless Steel | | 3 | | | | 2 | | |
| Brushed Nickel | | 3 | | | | 3 | | |
| Total # of marks on all (17) | | 9 | 5 | 2 | | 9 | 5 | 2 |

CHART 6-continued

For the test with bleach wipes, the following are the results for ghost marks showing in complete darkness using the Stylus UV flashlight and the Large Fluorescent Lamp.

|  | D1 | D2 | H | D1 | D2 | H |
|---|---|---|---|---|---|---|
|  | Bleach wipes | | | Bleach wipes | | |
| Total # of marks on nonporous (13) | 8 | 3 | 1 | 8 | 3 | 1 |
| Sum on nonporous | 17 | 4 | 1 | 16 | 5 | 1 |
| Total # of marks on metals (6) | 4 | 0 | 0 | 4 | 0 | 0 |
| Total # of marks on hard surfaces (7) | 4 | 3 | 1 | 4 | 3 | 1 |

Formula H did not do very well with this cleaner. This was consistent for both metals and hard surfaces. The interaction was strong on metals and laminate but very light on the rest of the hard surfaces.

Formula D1 did not do very well with this cleaner. This was only on hard surfaces and not on metals. The interactions were light.

Formula D2 did pretty good. There were marks only on the hard surfaces and not on metal. The marks were very light on laminate.

(Peroxide/Peracetic Acid)

CHART 7

For the test with Peroxyacetic acid, the following are the results for ghost marks showing in complete darkness using the Stylus UV flashlight and the Large Flourescent Lamp.

|  |  | D1 | D2 | H |  | D1 | D2 | H |
|---|---|---|---|---|---|---|---|---|
|  |  | Peroxyacetic acid | | | | Peroxyacetic acid | | |
| Zinc plated | Pen | 1 |  |  | Large | 1 |  |  |
| Brushed nickel | light | 2 | 5 | 2 | fluo- | 2 | 5 | 2 |
| laminate |  | 3 | 1 | 1 | res- | 3 | 2 | 2 |
| chrome |  |  |  |  | cent |  |  |  |
| Engravers brass |  |  |  |  |  | 1 |  |  |
| 50% ABS |  | 2 |  |  |  | 2 |  |  |
| 75% ABS |  | 2 |  |  |  | 2 |  |  |
| Stainless Steel |  |  |  |  |  |  |  |  |
| ABS textured |  | 3 | 2 |  |  | 4 | 3 |  |
| Total # of marks on all (9) |  | 6 | 3 | 2 |  | 7 | 3 | 2 |
| Sum on nonporous |  | 13 | 8 | 3 |  | 15 | 10 | 4 |
| Total # of marks on metals (5) |  | 2 | 1 | 1 |  | 3 | 1 | 1 |
| Total # of marks on hard surfaces (4) |  | 4 | 2 | 1 |  | 4 | 2 | 1 |

Formula H did not do well with this cleaner. The marks were apparent on both metal and hard surfaces. There were strong interactions with ABS and laminate.

Formula D1 had only a few marks but they were strong on ABS and light on laminate. The interaction on brushed nickel was very strong.

Formula did well on this formula with light interactions with brushed nickel and laminate.

Summary

In this study it was shown that on highly porous surfaces (marble or granite), it is very difficult to remove the fluorescent marks. This is regardless of what cleaning composition or fluorescent formula was used. In general, it has also been found that surfaces that are older and damaged from wear and tear or cleaning compositions are also more likely to leave ghost marks.

Overall, the D2 formula outperformed the other two formulas for both amount of ghost marks and intensity of ghost marks for all cleaning solutions. Since there are still a few difficult areas that ghost marks occur for the D2 formula, it is suggested to continue optimizing the formula.

The first generation D2 formula performed as expected. The anionic optical brightener is the free negative charge in the formula; therefore it is available to complex with any positively charged material that would remain on the surfaces. The worst results for this formula were with the Quat Disinfectant Cleaner, which leaves a positively charged residue on the surface. The best results were those that had negatively charged surfaces, such as that cleaned with water only. Although the amount and intensity of the second generation ghost marks were reduced, the same compatibility was seen as summarized above. Therefore, the anionic brightener in this formula may not be completely complexed.

The only unusual data that was generated pertains to Virasept and the negative interaction with both first generation and second generation D2 formulas. Since the ghost marks were primarily on hard surfaces and not metals, it might be possible that this isn't a situation of residual building up. It is unknown exactly what the cause of this interaction derived from. It may be possible there was a surface modification caused by the cleaners.

Conclusion

The results discussed in the summary section supports the concept of needing to complex the optical brightener with an agent of the opposite charge. This agent should be chosen to form a relatively strong complex with the optical brightener and other ingredients to help easily remove the mark from various surfaces.

Although the above discussion disclosed various exemplary embodiments of the invention, it should be apparent that those skilled in the art can make various modifications that will achieve some of the advantages of the invention without departing from the true scope of the invention.

EXAMPLE 4

Rating System

The tiles are observed under the specified lighting conditions using the different UV light sources. The rating was limited to one judge due to the time requirement of reading all the tiles. The tiles were read in random order and UV lights were used in random order. All tiles were read twice to confirm original judging. The rating was based on a scale of 0-5. The rating of 0 was given when there was absolutely no visible ghosting from any angle. A very faint mark was given a rating of 1 and was usually given when only a partial circular mark was apparent. This may also have been very faint in appearance, even to the experienced grader. Ratings of 2-5 were based on intensity of fluorescence. Occasionally, there would not be a full circular mark with the higher ratings but the UV intensity would still be intense.

Fluorescent Marking Gel formulas

TABLE 12

Representative Composition of the Invention 9C (Cationic optical brightener with complexing agent)

| Quantity | Description |
|---|---|
| 73.00 | Water DI |
| 2.00 | Leucophor FTS liq. |
| 20.00 | Versaflex One |
| 5.0 | Isopropyl Alcohol 99% |

Results

| | | Complete Dark | |
|---|---|---|---|
| | | 9C Water | 9C Water |
| Laminate countertop | | | |
| Shiny nickel | Pen light | 1 | Large Fluorescent |
| zinc plated | | 1 | |
| Engravers Brass | | | |
| 50% ABS | | | |
| 75% ABS | | | |
| marble | | 3 | 4 |
| granite | | 2 | 2 |
| black ceramic tile | | | |
| white ceramic tile | | | |
| ABS textured | | | 1 |
| Aluminum | | | |
| Polystyrene | | | |
| polypropylene | | | |
| laminate | | | 1 |
| Stainless Steel | | | |
| Brushed Nickel | | | |

Conclusion

The above testing was performed on a surface that has a negative charge remaining, which is the case when cleaned with water only. The formula was compatible with the surface because the cationic optical brightener was complexed with the anionic complexing agent. This further supports the theory that the optical brightener must be complexed or interaction will occur, as seen in Example 3.

What is claimed is:

1. A composition for determining whether a surface has been cleaned comprising:
   from about 0.001 weight % to about 20 weight % a cationic or anionic optical brightener;
   an oppositely charged complexing agent; and
   0.05 to 0.5 weight % preservative.

2. The composition of claim 1 wherein said optical brightener is an anionic optical brightener and the complexing agent is cationic.

3. The composition of claim 2, wherein:
   the surfactant is a nonionic surfactant;
   the cationic complexing agent is a quaternary diol;
   the solvent is an alcohol;
   the anionic optical brightener fluoresces under ultraviolet radiation; and
   the preservative is an isothiazolinone derivative.

4. The composition of claim 1 wherein said optical brightener is cationic and said complexing agent is anionic.

5. The composition of claim 1 wherein said cationic or anionic optical brightener comprises from about 0 weight % to about 5 weight % of the composition, and the oppositely charged complexing agent comprises from about 0 weight % to about 10 weight % with the remainder being water.

6. The composition of claim 5, wherein:
   the surfactant is an alcohol alkoxylate;
   the cationic complexing agent is dialkyloyl ethyldimonium salt
   the solvent is isopropyl alcohol;
   the anionic optical brightener is distyrylbiphenyl derivative; and
   the preservative is chloro methyl isothiazolin.

7. The composition of claim 1 wherein said complexing agent is selected from the group consisting of: surfactants, modified celluloses, modified guar, modified acrylic compounds, modified urethane, PVP, and ethoxycaboxylates.

8. The composition of claim 1 further comprising a solvent.

9. The composition of claim 1 further comprising a surfactant.

10. The composition of claim 1 comprising;
   a. to 20 weight % surfactant;
   b. 0 to 10 weight % complexing agent
   c. to 40.0 weight % solvent;
   d. to 5.0 weight % optical brightener; with the remainder being water.

11. The composition of claim 1, wherein the composition is substantially transparent after application to a surface.

12. The composition of claim 1, further comprising a thickener.

13. The composition of claim 1, wherein the viscosity of the composition is suitable for application with a felt tipped pad or foam applicator pad.

14. The composition of claim 1, wherein the composition is removable from a surface using water.

15. The composition of claim 1, wherein the composition is visible in the presence of ultraviolet radiation after application to a surface.

16. A composition for determining whether a surface has been cleaned comprising:
   from about 0.001 weight % to about 20 weight % a cationic or anionic optical brightener;
   an oppositely charged complexing agent; and
   from about 0 to about 5 weight % thickening agent.

17. A composition for monitoring a cleaned surface comprising:
   0.001 to 10.0 weight % surfactant;
   0.001 to 40 weight % solvent;
   0.01 to 7 weight % cationic dye/optical brightener, which fluoresces under ultraviolet radiation;
   0.07 to 0.3 weight % preservative;
   with the remainder being water.

* * * * *